(12) United States Patent
Buchanan et al.

(10) Patent No.: US 8,754,276 B2
(45) Date of Patent: Jun. 17, 2014

(54) REVERSE FLOW REACTORS FOR PROPYLENE AND AROMATICS PRODUCTION

(75) Inventors: John Scott Buchanan, Flemington, NJ (US); Stephen Mark Davis, Humble, TX (US); Frank Hershkowitz, Basking Ridge, NJ (US); John Slocum Coleman, Fairfax, VA (US); Seth McConkie Washburn, Houston, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 13/571,682

(22) Filed: Aug. 10, 2012

(65) Prior Publication Data

US 2014/0046107 A1 Feb. 13, 2014

(51) Int. Cl.
*C07C 5/32* (2006.01)

(52) U.S. Cl.
USPC .......... 585/324; 585/322; 585/407; 585/602; 585/634; 585/654; 208/66; 208/134

(58) Field of Classification Search
USPC ......... 585/311, 324, 319, 440, 444, 445, 616, 585/633, 634, 654, 660–663; 208/133–140; 422/171, 175, 206, 208, 211, 212, 220, 422/223
See application file for complete search history.

(56) References Cited

U.S. PATENT DOCUMENTS

| | | | |
|---|---|---|---|
| 4,704,497 A | | 11/1987 | Gottlieb et al. |
| 5,378,142 A | * | 1/1995 | Kennelly et al. ............ 431/7 |
| 5,510,557 A | | 4/1996 | Gartside et al. |
| 5,516,961 A | * | 5/1996 | Miller et al. .............. 585/660 |
| 5,899,678 A | * | 5/1999 | Thomson et al. .............. 431/2 |
| 7,498,473 B2 | * | 3/2009 | Zhou et al. ............... 585/417 |
| 7,815,873 B2 | | 10/2010 | Sankaranarayanan et al. |
| 7,846,401 B2 | | 12/2010 | Hershkowitz et al. |
| 2008/0142409 A1 | | 6/2008 | Sankaranarayanan et al. |
| 2008/0300438 A1 | | 12/2008 | Keusenkothen et al. |

FOREIGN PATENT DOCUMENTS

WO 02015965 7/2002

OTHER PUBLICATIONS

Hideshi Hattori, "Heterogeneous Basic Catalysis," 1995, Chemical Reviews, vol. 95, pp. 537-538.*
M. Van Sint Annaland, H.A.R. Scholts, J.A.M. Kuipers and W.P.M. Van Swaaji, "A novel reverse flow reactor coupling endothermic and exothermic reactions. Part I: comparison of reactor configurations for irreversible endothermic reactions", Chemical Engineering Science, 2002, pp. 833-854, vol. 57, issue 5.

(Continued)

*Primary Examiner* — In Suk Bullock
*Assistant Examiner* — Candace R Chouinard
(74) *Attorney, Agent, or Firm* — Robert A. Migliorini (57) ABSTRACT

A reverse flow regenerative reactor having first and second zones, each having first and second ends, the first zone having a plurality of channels capable of separately conveying at least two components of a combustible gas mixture, a gas distributor configured for injecting the components of the combustible gas mixture into first zone, a combustion zone including a selective combustion catalyst disposed at or downstream of the second end of said channels for catalyzing combustion, wherein the second zone is positioned and situated to receive a combusted gas mixture. Processes usefully conducted in the reactor are also disclosed.

15 Claims, 4 Drawing Sheets

(56) References Cited

OTHER PUBLICATIONS

M. Van Sint Annaland, H.A.R. Scholts, J.A.M. Kuipers and W.P.M. Van Swaaji, "A novel reverse flow reactor coupling endothermic and exothermic reactions. Part II: Sequential reactor configurations for reversible endothermic reactions", Chemical Engineering Science, 2002, pp. 855-872, vol. 57, issue 5.

M. Van Sint Annaland and R.C. Nijssen, "A novel reverse flow reactor coupling endothermic and exothermic reactions: an experimental study", Chemical Engineering Science, 2002, pp. 4967-4985, vol. 57, issues 22-23.

M. Van Sint Annaland, J.A.M. Kuipers and W.P.M. Van Swaaij, "Safety analysis of switching between reductive and oxidative conditions in a reaction coupling reverse flow reactor", Chemical Engineering Science, 2001, pp. 1517-1524, vol. 56, issue 4.

C. Ercan and R.J. Gartside, "Reactor performance and stability in an alternating reaction-reheat paraffin dehydrogenation system", The Canadian Journal of Chemical Engineering, 1996, pp. 626-637, vol. 74, issue 5.

Y.S. Matros and G.A. Bunimovich, "Reverse-flow operation in fixed bed catalytic reactors", Catalysis Reviews—Science and Engineering, 1996, pp. 1-8, vol. 38, issue 1.

* cited by examiner

REVERSE FLOW REACTORS FOR PROPYLENE AND AROMATICS PRODUCTION

FIELD

The present disclosure is directed to improved methods for "on-purpose" propylene and aromatics manufacture which have lower cost, higher efficiency and product selectivity.

BACKGROUND

Propylene co-products from ethylene steam crackers and from fluidized catalytic cracking (FCC) have been the traditional sources of propylene for the past decades. With a high rate of growth in polypropylene uses, demand for propylene is exceeding the supply available from these traditional sources.

Reverse Flow Reactor (RFR) technology has been the subject of much development over the last 10 years, but mostly as applied to higher temperature reactions such as methane pyrolysis and steam reforming.

U.S. Pat. No. 4,704,497 to Gottlieb et al. discloses a process for dehydrogenating saturated or unsaturated hydrocarbons wherein the flow direction of the oxygen-containing gas, employed for removing coke deposits on the catalyst surface, is opposite to that for the hydrocarbon feed undergoing dehydrogenation.

U.S. Pat. No. 5,510,557 to Gartside et al. discloses catalytic dehydrogenation wherein feed is passed in one direction through the bed in a first cycle and heating gas is passed in an opposite direction in a second cycle to provide the endothermic heat of reaction and regenerate catalyst. The operation is controlled to properly balance heat absorbed during dehydrogenation and heat input during regeneration; e.g., by having catalyst of different activities over the length of the bed.

U.S. Pat. No. 7,815,873 to Sankaranarayanan et al. discloses the overall efficiency of a regenerative bed reverse flow reactor system is increased where the location of the exothermic reaction used for regeneration is suitably controlled. The disclosure provides a method and apparatus for controlling the combustion to improve the thermal efficiency of bed regeneration in a cyclic reaction/regeneration processes. The process for thermal regeneration of a regenerative reactor bed entails (a) supplying the first reactant through a first channel means in a first regenerative bed and supplying at least a second reactant through a second channel means in the first regenerative bed, (b) combining said first and second reactants by a gas mixing means situated at an exit of the first regenerative bed and reacting the combined gas to produce a heated reaction product, (c) passing the heated reaction product through a second regenerative bed thereby transferring heat from the reaction product to the second regenerative bed.

U.S. Pat. No. 7,846,401 to Hershkowitz et al. discloses increasing the overall efficiency of a regenerative bed reverse flow reactor system where the location of the exothermic reaction used for regeneration is suitably controlled. The disclosure provides a method and apparatus for controlling the combustion to improve the thermal efficiency of bed regeneration in a cyclic reaction/regeneration processes. The process for thermal regeneration of a regenerative reactor bed entails (a) supplying the first reactant through a first channel means in a first regenerative bed and supplying at least a second reactant through a second channel means in the first regenerative bed, (b) combining said first and second reactants by a gas mixing means situated at an exit of the first regenerative bed and reacting the combined gas to produce a heated reaction product, (c) passing the heated reaction product through a second regenerative bed thereby transferring heat from the reaction product to the second regenerative bed.

U.S. Published Patent Application No. 2008/0300438 to Keusenkothen et al. discloses a process for pyrolyzing a hydrocarbon feedstock containing nonvolatiles in a regenerative pyrolysis reactor system. The process comprises: (a) heating the nonvolatile-containing hydrocarbon feedstock upstream of a regenerative pyrolysis reactor system to a temperature sufficient to form a vapor phase that is essentially free of nonvolatiles and a liquid phase containing the nonvolatiles; (b) separating said vapor phase from said liquid phase; (c) feeding the separated vapor phase and methane to the pyrolysis reactor system; and (d) converting the methane and separated vapor phase in said pyrolysis reactor system to form a pyrolysis product. In another aspect, the disclosure includes a separation process that feeds multiple pyrolysis reactors.

World Patent No. 2002/051965 A1 to Van de Beld discloses a method of carrying out a cracking reaction in a packed-bed reverse flow reactor. For the purpose of maintaining the temperature of the reverse flow reactor, a less than stoichiometric amount of oxygen is added to a combustible gas comprising a compound to be cracked. According to the disclosure, there is a mixing chamber between two packed beds into which oxygen is supplied. The disclosure also describes a preferred embodiment, in which a mixing chamber is provided between three beds, which in time periodically fulfill a different role.

"A Novel Reverse Flow Reactor Coupling Endothermic And Exothermic Reactions", parts I and II to M. van Sint Annaland et al., *Chemical Engineering Science*, 57, (2002), pp. 833-854 (part I) and pp. 855-872 (part II), discloses a reactor concept for highly endothermic heterogenously catalysed gas phase reactions at high temperatures with rapid but reversible catalyst deactivation, by indirect coupling of energy necessary for endothermic reactions, such as propane dehydrogenation, and energy released by exothermic reactions, without mixing of the endothermic and exothermic reactants, in a closed-loop reverse flow operation. Two different reactor configurations are considered: a sequential reactor configuration, where the endothermic and exothermic reactants are fed sequentially to the same catalyst bed acting as an energy repository, and a simultaneous reactor configuration, wherein the endothermic and exothermic reactants are fed continuously to two different compartments directly exchanging energy.

"A Novel Reverse Flow Reactor Coupling Endothermic And Exothermic Reactions: An Experimental Study", to M. van Sint Annaland et al., *Chemical Engineering Science*, 57, (2002), pp. 4967-4985, discloses an experimental study of propane dehydrogenation coupled with methane combustion over a monolithic catalyst, in which back-conversion of propylene to propane is minimized by adding inactive sections flanking the catalyst at both ends.

The potential application of these reactors to lower-temperature chemistry has been speculated upon, but the details have not been developed. Accordingly, advances in RFR technology and processes are needed to enhance the effectiveness of the technology.

SUMMARY

In a first embodiment, the present disclosure is directed to a reverse flow regenerative reactor, comprising a first zone having a plurality of channels having first and second ends, the channels capable of separately conveying at least two components of a combustible gas mixture through the first zone, a gas distributor disposed proximate to the first end of the plurality of channels for injecting the at least two components into the first end of the channels within the first zone, a combustion zone disposed at or downstream of the second end of the channels, the combustion zone comprising a selective combustion catalyst for catalyzing combustion of the two components, and a second zone having first and second ends and situated to receive a combusted gas mixture.

The reverse flow regenerative reactor preferably has a selective combustion catalyst disposed in a selective combustion catalyst bed between the first and second zones, such as being disposed as a coating on a short section of the second end of the channels of the first zone, or as a coating on a short section of the first end of the second zone.

In a preferred embodiment, the second zone comprises a dehydrogenation catalyst disposed therein, for example where the second zone comprises a plurality of channels having first and second ends, and a dehydrogenation catalyst disposed along and within at least a portion of the channels.

Advantageously, the gas distributor is configured to inject the two components into the first ends of mutually separate channels of the first zone, and the selective combustion catalyst is disposed in a selective combustion catalyst bed between the first and second zones, or the selective combustion catalyst can be disposed as a coating on a short section at the first end of the second zone, or the selective combustion catalyst can be disposed as a coating on a short section of the second ends of the channels of the first zone.

In a preferred embodiment, the selective combustion catalyst comprises oxides of metals in columns IIIB through VA of the periodic table, including lanthanides, and combinations thereof, and is more preferably a basic catalyst.

Advantageously, the combustion zone further comprises an inert packing or support, capable of retaining heat, and the channels of the first and second zones comprise ceramics.

Another embodiment of the present disclosure is directed to a process comprising providing a reverse flow regenerative reactor comprising separate first and second zones, both of the first and second zones having first and second ends, and wherein the first zone is configured to transfer heat to or from gases passing therethrough, and at least a portion of the second zone comprises a dehydrogenation catalyst, passing at least two components of a combustible gas mixture in a first direction through the first zone, combusting the combustible gas mixture with the aid of a selective combustion catalyst disposed in a combustion zone at or downstream of the second end of the first zone to form hot combustion products, passing the hot combustion products through the second zone to transfer heat from the hot combustion products to the dehydrogenation catalyst, so as to heat the dehydrogenation catalyst to a selected temperature, and exhausting the combustion products from the second zone.

The process can further comprise terminating gas flow in the first direction, passing a hydrocarbon feed comprising $C_1$-$C_{10}$ hydrocarbons in a direction opposite the first direction and into the second end of the second zone, dehydrogenating at least a portion of the hydrocarbon feed within the second zone to form one or more dehydrogenated hydrocarbon products, passing the dehydrogenated hydrocarbon products into the second end of the first zone and quenching the dehydrogenated hydrocarbon products, and recovering the dehydrogenated hydrocarbon products from the first end of the first zone.

Advantageously, the dehydrogenation catalyst used in the process comprises Group VB metals, Group VIB metals, Group VIII metals, Group VIII metal alloys with Group IB metals, or oxides thereof, and the dehydrogenation process can be conducted at a selected temperature from 625° C. to 800° C., and a pressure from 1 to 5 atmospheres.

When the hydrocarbon feed for the process is propane, the dehydrogenated hydrocarbon product is propylene, or when the hydrocarbon feed is butane, the dehydrogenated hydrocarbon product is butenes and/or butadiene.

Alternatively the dehydrogenation process can be a dehydrocyclodimerization process, wherein the hydrocarbon feed is $C_1$ to $C_{10}$ paraffins or olefins, which further comprises dimerizing or further oligomerizing the dehydrogenated hydrocarbon product(s) to form aromatic hydrocarbons. Under these circumstances a dehydrocyclodimerization catalyst is disposed on a support within the second zone, such as a catalyst comprising a medium-pore molecular sieve such as ZSM-5, promoted with a dehydrogenation function such as Ga, Pt, Zn, In, Pd, Ir, Mo or combinations thereof.

Additionally, the hydrocarbon feed to the process can be light virgin naphtha having $C_4$-$C_{10}$ paraffins, and hydrogen derived from the dehydrogenation step can be recycled to the reaction to improve selectivity of the reaction step for various products, and wherein naptha conversion further comprises cracking to increase the yield of light olefins in the product In preferred embodiments, the selective combustion catalyst is disposed on the channels at the second end of the first zone, and the two components of the combustible gas mixture are passed through the first zone as a mixture, or the selective combustion catalyst is disposed in a catalyst bed downstream of the second end of the first zone, and the two components of the combustible gas mixture are separately passed through the first zone in mutually exclusive channels, or the selective combustion catalyst is disposed on a support at the first end of the second zone, separated from and upstream of the dehydrogenation catalyst portion, and the two components of the combustible gas mixture are separately passed through the first zone in mutually exclusive channels.

Advantageously, the selective combustion catalyst comprises oxides of metals in columns IIIB through VA of the periodic table, including lanthanides, and combinations thereof, and the selective combustion catalyst is a basic catalyst.

Preferably, in the process of this embodiment, the combustion zone further comprises an inert packing or support, capable of retaining heat, and the channels of the first and second zones comprise ceramics.

DETAILED DESCRIPTION

All numerical values within the detailed description and the claims herein are modified by "about" or "approximately"

the indicated value, and take into account experimental error and variations that would be expected by a person having ordinary skill in the art.

In the present disclosure, variations of RFR technology are applied to paraffin dehydrogenation and dehydrocylization. The rapid cycle RFR reactor offers a number of advantages, including compact design, excellent heat integration, and operation at higher than conventional temperatures. Operation at higher temperature enables operation at higher conversion and at higher pressure, both of which result in significantly improved process economics.

However, for the present applications, which are advantageously conducted at lower temperatures than previously-developed steam reforming RFR, added means are provided to ensure a high level of combustion during the heat-regeneration step. For example, a selective combustion catalyst zone is added, to maintain a preferred temperature profile in the main catalyst bed.

We focus here on propane dehydrogenation, but this disclosure is applicable to other endothermic reactions including dehydrogenation of other light paraffins, e.g. $C_1$-$C_6$ paraffins. Propane dehydrogenation to propylene creates a valuable olefin product from less expensive paraffins, but is thermodynamically limited. This necessitates expensive separation schemes and large recycle streams to achieve high overall propane conversions. To decrease the size of the required recycle, and thus greatly improve the economics of propane dehydrogenation, several methods are used to increase the equilibrium propane-to-propylene conversion and thus increase the single pass conversion.

A reverse flow reactor (RFR) has an advantage of reaching high internal temperatures while maintaining relatively cool reactor ends. This is done by cycling the reactor in a counter-current configuration through a period of propane dehydrogenation followed by a separate period of combustion with air and fuel.

Figure 1A:
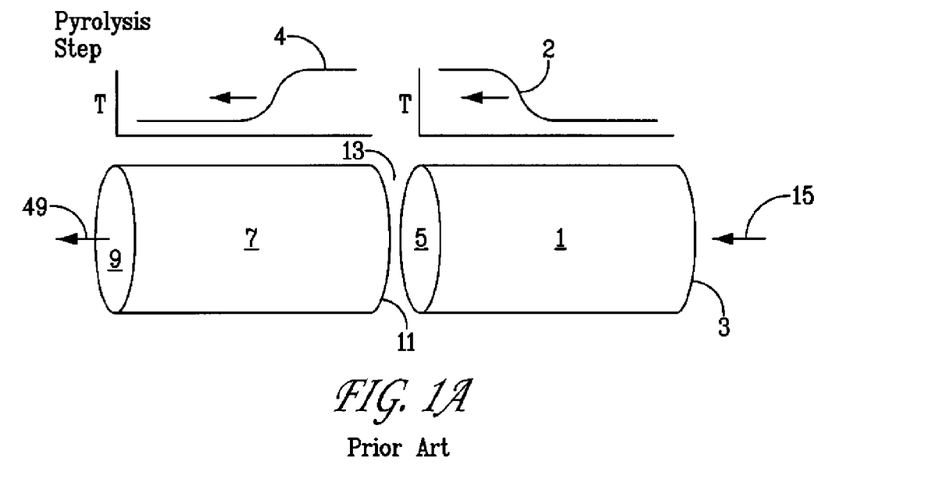
FIGS. 1A and 1B are simplified, diagrammatic illustrations of the two steps in a prior art regenerative reverse flow reactor system.
Figure 1B:
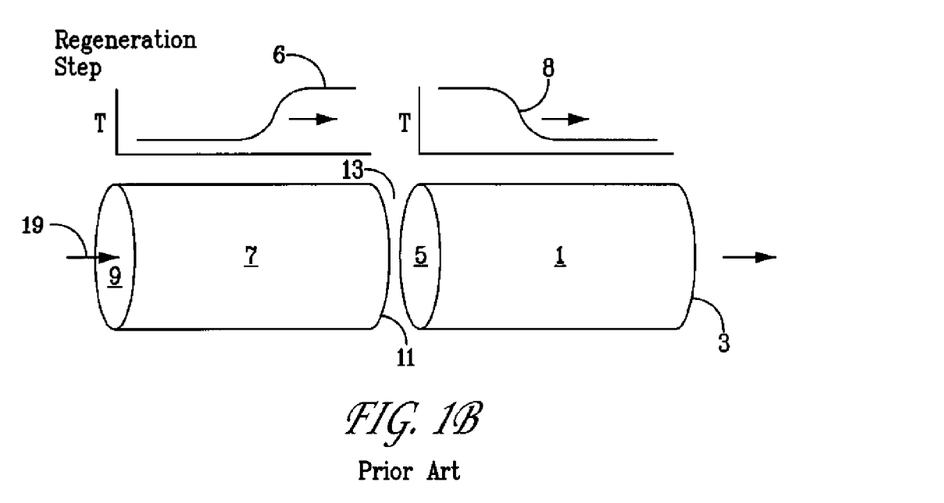

The basic two-step asymmetric cycle of a regenerative bed reactor system is depicted in FIGS. 1A and 1B in terms of a reactor system having two zones; a first or recuperator/quenching zone 7 and a second or reaction/reforming zone 1. Both the reaction zone 1 and the recuperator zone 7 contain regenerative beds of a regenerative media. The regenerative beds may comprise bedding or packing material that is effective in storing and transferring heat, such as glass or ceramic beads or spheres, metal beads or spheres, ceramic (e.g., ceramics, which may include alumina, yttria, and zirconia) or metal honeycomb materials, ceramic tubes, extruded monoliths and the like, provided they are competent to maintain integrity, functionality, and withstand long term exposure to temperatures in excess of 700° C., in excess of 800° C., or even in excess of 1000° C. for operating margin.

As shown in FIG. 1A, at the beginning of the "reaction" step of the cycle, a secondary end 5 of the reaction zone 1, which may be referred to as the reformer or second reactor, is at an elevated temperature as compared to the primary end 3 of the reaction zone 1, and at least a portion, including the first end 9 of the recuperator or quench zone 7 is at a lower temperature than the reaction zone 1, to provide a quenching effect for the reaction products. A hydrocarbon containing reactant feed, and preferably also a diluent or stripping agent, such as hydrogen or steam, is introduced via a conduit(s) 15, into a primary end 3 of the reforming or reaction zone 1.

The feed stream from inlet(s) 15 absorbs heat from the refractory bed in reaction zone 1 and endothermically reacts to produce a desired unsaturated hydrocarbon product, such as light olefins. As this step proceeds, a shift in the temperature profile 2, as indicated by the arrow, is created based on the heat transfer properties of the system. When the bed is designed with adequate heat transfer capability, this profile has a relatively sharp temperature gradient, which gradient moves across the reaction zone 1 as the step proceeds. The sharper the temperature gradient profile, the more control provided for the reaction.

The reaction products exit the reaction zone 1 through a secondary end 5 at an elevated temperature and pass into the recuperator reactor 7 through a second end 11, and exits at a first end 9 as a reaction product 49 typically comprising light olefins (e.g. propylene). As the reaction products pass through the recuperator zone 7, the reaction products transfer heat to the regenerative bed in the recuperator zone and are quenched or cooled to a temperature approaching the temperature of the recuperator zone substantially at the first end 9, which in some embodiments is preferably approximately the same temperature as the regeneration (combustion) feed introduced via conduit 19 into the recuperator 7 during the second step (FIG. 1B) of the cycle. As the reaction gas is cooled in the recuperator zone 7, a temperature gradient 4 is created in the zone's regenerative bed(s) and moves across the recuperator zone 7 during this step. After quenching, the reaction product exits the recuperator zone at 9 and is processed for separation and recovery of the various components.

The second step of the cycle (FIG. 1B), referred to as the regeneration step, then begins with reintroduction of the first and second regeneration reactants (e.g. air and fuel gas) via separated conduits or channels 19 within, for example, the honeycomb reactor bedding material, which has at least one first channel and one second channel which are separated by a barrier that prevents at least a majority of a stoichiometrically reactable first reactant from reacting with the second reactant within the recuperator zone 7. Preferably when the reactor bed is in the form of a honeycomb, some channels through the structure are dedicated to the first reactant, while the others are dedicated to the second reactant. The first and second combustion reactants pass separately through hot recuperator zone 7 toward the second end 11 of the recuperator zone, where they exothermically react or combust in or near a central mixing/combustion zone 13 of the reactor system. During this step, the temperature gradients 6 and 8 move across the beds as illustrated by the arrows on the exemplary graphs in FIG. 1B, similar to but in opposite directions to the temperature gradients developed during the reaction cycle in FIG. 1A. The heat recovered from the recuperator zone together with the heat of combustion in combustion zone 13 is transferred to reaction zone 1, thermally regenerating the regenerative reaction beds disposed therein.

For a reversible endothermic reaction like dehydrogenation, it is highly desirable to have the highest temperature in the catalyst bed be at the exit of the reaction bed 5. For an active catalyst, the extent of final conversion will be largely set by the temperature at the exit. Thus, it is important to design RFR hardware and operations to ensure this sort of temperature profile.

For processes that run hotter, e.g. steam reforming at around 1100° C., the air/fuel mixture combusts quickly and homogeneously as soon as it is mixed, before it enters the catalyst bed. This has the effect of enforcing the desired temperature profile 8.

Figure 1C:
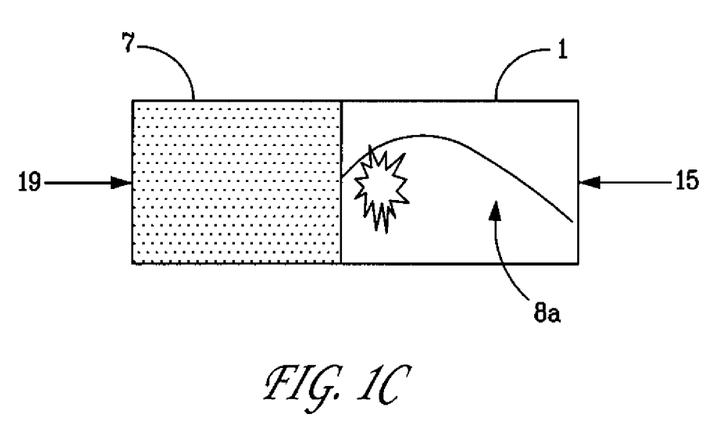
FIG. 1C is a schematic representation of operation of a prior art reverse flow reactor system under conditions appropriate for dehydrogenation of paraffins.

However, when operating at around 700° C. for paraffin dehydrogenation, and with the preferred methane fuel gas, it is possible that some uncombusted air/fuel mixture could penetrate the bed 1 of dehydrogenation catalyst, where the catalyst would then catalyze the combustion deep within reaction bed 1, such that a substantial portion of the fuel gas is combusted within the catalyst bed 1. If that happens, the peak temperature in bed 1 may move away from the catalyst zone exit 5, and an average temperature profile 8a can develop where the temperature is highest in the middle of the catalyst bed 1 (FIG. 1C), resulting in cooler catalyst zone exit when flow reverses. In such cases, as the reaction gas mixture continues towards the exit of the dehydrogenation catalyst bed, it encounters a zone where the temperature has declined. This will tend to reverse the conversion that had been attained earlier. This is highly undesirable.

In the present disclosure (FIG. 2), a short bed of selective combustion catalyst 10 is positioned between the main dehydrogenation catalyst bed 1 and the fuel/air mixer 7. The function of this selective combustion zone is to initiate combustion of the fuel gas to help enforce a monotonically rising temperature profile 8b in the dehydrogenation catalyst bed 1, as will be seen by the paraffin feed upon reversal of the reactor flow. A monotonic temperature profile eliminates the undesirable reversal of paraffin dehydrogenation that can occur if the end temperature of the catalyst bed 1 decreases below the equilibrium temperature for the gas phase paraffin content.

Also, introducing a selective combustion bed provides an additional means to manipulate and optimize the performance of a reverse flow reactor for dehydrogenation. For instance, with the selective combustion bed in place as described here, the ratio of air/fuel flow rate to propane feed rate into the reactor can be independently manipulated without disrupting the desired monotonic temperature profile.

According to the present disclosure, a reverse flow regenerative reactor is provided comprising a first zone having a plurality of channels having first and second ends, the channels capable of separately conveying at least two components of a combustible gas mixture through the first zone, a gas distributor disposed proximate to the first end of the plurality of channels for injecting the at least two components into the first end of the channels within the first zone, a combustion zone disposed at or downstream of the second end of the channels, the combustion zone comprising a selective combustion catalyst for catalyzing combustion of the two components, and a second zone having first and second ends and situated to receive a combusted gas mixture.

Figure 2:
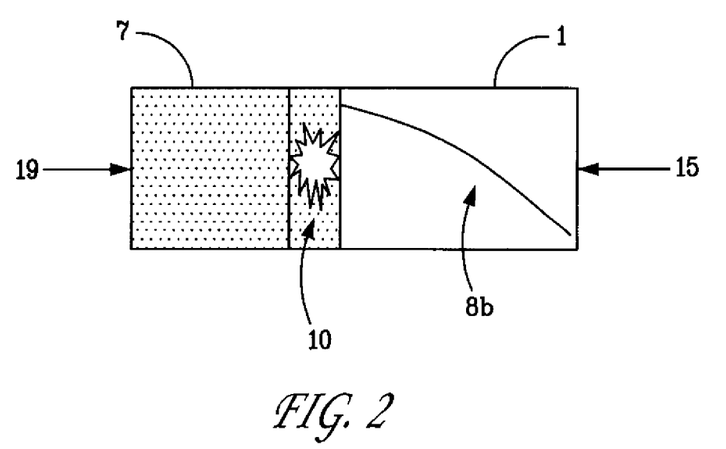
FIG. 2 is a schematic representation of the modified reverse flow reactor of according to the present disclosure.

In FIG. 2, a relatively thin zone of selective combustion catalyst 10 has been added between the active bed of dehydrogenation catalyst 1, and the usual bed of substantially inert packing 7 that is used in the reverse flow reactor to capture and re-use heat. The absolute value of the minimum combustion catalyst activity will depend on the fraction of the reactor length that is dedicated to this selective combustion zone. Preferably the selective combustion zone 10 occupies less than 10% of the total internal reactor length or bed volume, and more preferably less than 5%. The activity of this catalyst must be sufficiently high to combust over 40%, preferably over 60%, and more preferably over 85% of the fuel gas within this selective combustion zone, before it enters the dehydrogenation catalyst bed. The function of this selective combustion zone is to initiate combustion of the fuel gas to help enforce a monotonically rising temperature profile 8b in the dehydrogenation catalyst bed 1, as will be seen by the paraffin feed. A monotonic temperature profile 8b will eliminate the undesirable reversal of paraffin dehydrogenation that can occur if the end temperature of the catalyst bed decreases below the equilibrium temperature for the gas phase paraffin content.

The selective combustion catalyst bed 10 is preferably disposed between the first and second zones of the RFR reactor, such as being disposed as a coating on a short section of the second end 11 of the channels of the first (recuperator) zone 7 (FIGS. 1a and 1b), or as a coating on a short section of the first end 5 of the second (catalytic) zone 1 (FIGS. 1a and 1b), or even as a separate catalyst bed. The selective combustion catalyst promotes the combustion of fuel in the presence of oxygen, but has relatively low activity in the dehydrogenation/hydrogenation reaction. Criteria for the ratio of combustion activity to hydrogenation activity are discussed below.

In a preferred embodiment, the selective combustion catalyst comprises oxides of metals in columns IIIB through VA of the periodic table, including lanthanides, and combinations thereof, and is more preferably a basic catalyst. The metals or metal oxides may be supported on a porous, thermally stable support. Some suitable supports include alumina, silica, zirconia, and magnesia. A basic, rather than acidic, catalyst is preferred, to reduce unwanted reactions such as cracking and coking. A basic species, including alkali or alkali earth, may be added to moderate undesired acidity. Optionally, the selective combustion oxide catalyst may comprise metals or oxides from Group VIII.

In a preferred embodiment, the second zone 1 comprises a dehydrogenation catalyst disposed therein, for example where the second zone comprises a plurality of channels having first and second ends, and a dehydrogenation catalyst disposed along and within at least a portion of the channels.

Advantageously, a gas distributor is configured to inject fuel and air components into the first ends of mutually separate channels of the first zone, and the selective combustion catalyst is disposed in a selective combustion catalyst bed between the first and second zones, or the selective combustion catalyst can be disposed as a coating on a short section at the first end of the second zone, or the selective combustion catalyst can be disposed as a coating on a short section of the second ends of the channels of the first zone.

When configured as a separate bed, the combustion catalyst bed 10 can further comprise an inert packing or support, capable of retaining heat, and the channels of the first and second zones comprise ceramics.

Another embodiment of the present disclosure is directed to a process comprising providing a reverse flow regenerative reactor comprising separate first and second zones, both of the first and second zones having first and second ends, and wherein the first zone is configured to transfer heat to or from gases passing therethrough, and at least a portion of the second zone comprises a dehydrogenation catalyst, passing at least two components of a combustible gas mixture in a first direction through the first zone, combusting the combustible gas mixture with the aid of a selective combustion catalyst disposed in a combustion zone at or downstream of the second end of the first zone to form hot combustion products, passing the hot combustion products through the second zone to transfer heat from the hot combustion products to the dehydrogenation catalyst, so as to heat the dehydrogenation catalyst to a selected temperature, and exhausting the combustion products from the second zone.

The process can further comprise terminating gas flow in the first direction, passing a hydrocarbon feed comprising $C_1$-$C_{10}$ hydrocarbons in a direction opposite the first direction and into the second end of the second zone, dehydrogenating at least a portion of the hydrocarbon feed within the second zone to form one or more dehydrogenated hydrocarbon products, passing the dehydrogenated hydrocarbon products into the second end of the first zone and quenching the dehydrogenated hydrocarbon products, and recovering the dehydrogenated hydrocarbon products from the first end of the first zone.

Advantageously, the dehydrogenation catalyst used in the process comprises Group VB metals, Group VIB metals, Group VIII metals. Group VIII metal alloys with Group IB metals, or oxides thereof, and the dehydrogenation process can be conducted at a selected temperature from 625° C. to 800° C., preferably from 675° C. to 725° C. and a pressure from 1 to 5 atmospheres, preferably from 1.5 to 3 atmospheres absolute.

When the hydrocarbon feed for the process is propane, the dehydrogenated hydrocarbon product is propylene, or when the hydrocarbon feed is butane, the dehydrogenated hydrocarbon product is butenes and/or butadienes.

Alternatively the dehydrogenation process can be a dehydrocyclodimerization process, wherein the hydrocarbon feed is $C_1$ to $C_{10}$ paraffins or olefins, which further comprises dimerizing or further oligomerization of the dehydrogenated hydrocarbon product(s) to form aromatic hydrocarbons. Under these circumstances a dehydrocyclodimerization catalyst is disposed on a support within the second zone, such as a catalyst comprising a medium-pore molecular sieve such as ZSM-5, promoted with a dehydrogenation function such as Ga, Pt, Zn, In, Pd, Ir, Mo or combinations thereof.

Additionally, the hydrocarbon feed to the process can be light virgin naphtha having $C_4$-$C_{10}$ paraffins, and hydrogen derived from the dehydrogenation step can be recycled to the reaction zone to improve selectivity of the reaction step for various products. When naphtha range feedstocks are utilized, conversion process may include cracking as well as dehydrogenation to increase the amount of lighter olefins in the reaction products.

In preferred embodiments, the selective combustion catalyst is disposed on channels at the second end of the first zone, and the two components of the combustible gas mixture are passed through the first zone as a mixture, or the selective combustion catalyst is disposed in a catalyst bed downstream of the second end of the first zone, and the two components of the combustible gas mixture are separately passed through the first zone in mutually exclusive channels, or the selective combustion catalyst is disposed on a support at the first end of the second zone, separated from and upstream of the dehydrogenation catalyst portion, and the two components of the combustible gas mixture are separately passed through the first zone in mutually exclusive channels.

Advantageously, the selective combustion catalyst comprises oxides of metals in columns IIIB through VA of the periodic table, including lanthanides, and combinations thereof, and the selective combustion catalyst is a basic catalyst. Optionally, the selective combustion catalyst may comprise Group VIII metals or oxides.

Preferably, in the process of this embodiment, the combustion zone further comprises an inert packing or support, capable of retaining heat, such as wherein the channels of the first and second zones comprise ceramics.

PCT and EP Clauses:

In a first embodiment, the disclosure is directed to a reverse flow regenerative reactor, comprising a first zone having a plurality of channels having first and second ends, said channels capable of separately conveying at least two components of a combustible gas mixture through said first zone: a gas distributor disposed proximate to the first end of the plurality of channels for injecting said at least two components into the first end of said channels within the first zone; a combustion zone disposed at or downstream of the second end of said channels, said combustion zone comprising a selective combustion catalyst for catalyzing combustion of said two components; and a second zone having first and second ends and situated to receive a combusted gas mixture.

In a second embodiment, the reverse flow regenerative reactor of the first embodiment can have the selective combustion catalyst disposed in a selective combustion catalyst bed between said first and second zones, or disposed as a coating on a short section of the second end of said channels of said first zone, or disposed as a coating on a short section of the first end of said second zone.

In a third embodiment, according to any of the above embodiments, said second zone can comprise a dehydrogenation catalyst disposed therein.

In a fourth embodiment, according to any of the above embodiments, said second zone can comprise a plurality of channels having first and second ends, and a dehydrogenation catalyst disposed along and within at least a portion of said channels.

In a fifth embodiment, the reverse flow regenerative reactor of the first embodiment can have said gas distributor configured to inject said two components into the first ends of mutually separate channels of said first zone, and said selective combustion catalyst is disposed in a selective combustion catalyst bed between said first and second zones, or said selective combustion catalyst is disposed as a coating on a short section at the first end of said second zone, or said gas distributor is configured to inject said two components as a mixture into the first ends of said channels of said first zone, and said selective combustion catalyst is disposed as a coating on a short section of the second ends of said channels of said first zone.

In a sixth embodiment, the reverse flow regenerative reactor of any of the preceding embodiments can have the selective combustion catalyst comprise oxides of metals in columns IIIB through VA of the periodic table, including lanthanides, and combinations thereof, and the selective combustion catalyst is preferably a basic catalyst.

In a seventh embodiment, when the combustion zone comprises a separate catalyst bed, it further comprises an inert packing or support, capable of retaining heat.

In an eighth embodiment, the reverse flow regenerative reactor of any of the preceding embodiments can be configured such that the channels of said first and/or second zones comprise ceramics.

A ninth embodiment of the present disclosure is directed to a process comprising providing a reverse flow regenerative reactor comprising separate first and second zones, both of said first and second zones having first and second ends, and wherein said first zone is configured to transfer heat to or from gases passing therethrough, and at least a portion of said second zone comprises a dehydrogenation catalyst, passing at least two components of a combustible gas mixture in a first direction through said first zone, combusting said combustible gas mixture with the aid of a selective combustion catalyst disposed in a combustion zone at or downstream of the second end of said first zone to form hot combustion products, passing said hot combustion products through said second zone to transfer heat from said hot combustion products to said dehydrogenation catalyst, so as to heat said dehydrogenation catalyst to a selected temperature, and exhausting said combustion products from said second zone.

In a tenth embodiment, the process of the ninth embodiment further comprises terminating gas flow in said first direction, passing a hydrocarbon feed comprising $C_1$-$C_{10}$ hydrocarbons in a direction opposite said first direction and into the second end of said second zone, dehydrogenating at least a portion of said hydrocarbon feed within said second zone to form one or more dehydrogenated hydrocarbon products, passing said dehydrogenated hydrocarbon products into the second end of said first zone and quenching said dehydrogenated hydrocarbon products, and recovering said dehydrogenated hydrocarbon products from the first end of said first zone.

In an eleventh embodiment, the process of the ninth or tenth embodiments are preferably conducted such that said dehydrogenation catalyst comprises Group VB metals, Group VIB metals, Group VIII metals, Group VIII metal alloys with Group IB metals, or oxides thereof.

In a twelfth embodiment, the dehydrogenation of the ninth to eleventh embodiments is conducted at a selected temperature from 625° C. to 800° C., and a pressure from 1 to 5 atmospheres absolute.

In a thirteenth embodiment, the processes of the ninth to twelfth embodiments is conducted such that the hydrocarbon feed is propane and said dehydrogenated hydrocarbon product is propylene, or such that the hydrocarbon feed is butane and said dehydrogenated hydrocarbon product is butenes and/or butadiene.

In a fourteenth embodiment, the process of the tenth embodiment is a dehydrocyclodimerization process, wherein said hydrocarbon feed is $C_1$ to $C_{10}$ paraffins, light virgin naphthas having $C_4$-$C_{10}$ paraffins or olefins, and further comprises cracking of the feed, and/or dimerizing or otherwise oligomerizing said dehydrogenated hydrocarbon product(s) to form aromatic hydrocarbons, such as where a dehydrocyclodimerization catalyst is disposed on a support within said second zone, and said dehydrocyclodimerization catalyst comprises a medium-pore molecular sieve such as ZSM-5, promoted with a dehydrogenation function such as Ga, Pt, Zn, In, Pd, Ir, Mo or combinations thereof.

In a fifteenth embodiment, the process of any of the tenth to the fourteenth embodiments can include recycling hydrogen derived from said dehydrogenation step to the reaction to improve selectivity of the reaction step for various products.

In a sixteenth embodiment, the processes of embodiments nine through fifteen can be conducted such that the selective combustion catalyst is disposed on said channels at the second end of said first zone, and said two components of said combustible gas mixture are passed through said first zone as a mixture, or such that the selective combustion catalyst is disposed in a catalyst bed downstream of the second end of said first zone, and said two components of said combustible gas mixture are separately passed through said first zone in mutually exclusive channels, or such that the selective combustion catalyst is disposed on a support at the first end of said second zone, separated from and upstream of said dehydrogenation catalyst portion, and said two components of said combustible gas mixture are separately passed through said first zone in mutually exclusive channels.

In a seventeenth embodiment, the processes of the ninth through sixteenth embodiments can use a selective combustion catalyst comprising oxides of metals in columns IIIB through VA of the periodic table, including lanthanides, and combinations thereof, especially wherein the selective combustion catalyst is a basic catalyst.

In an eighteenth embodiment, the ninth embodiment can be conducted such that the combustion zone further comprises an inert packing or support, capable of retaining heat, and wherein the channels of said first and second zones comprise ceramics.

EXAMPLES

Example 1

Prior Art

A quantitative example is now discussed. A model was developed for tracking the transient flows, reactions, and heat transfer in a reverse flow reactor. In the base case (FIGS. 3A and 3B), the dehydrogenation catalyst bed fills the reactor from position x=0.25 to x=0.75, where x is the fractional reactor position. The remainder of the reactor (x<0.25 and x>0.75) is filled with inerts that mainly function to recover heat. In the discussions from now on, air and fuel are considered to come in from the left (x=0), and feed (propane) to come in from the right (x=1).

For the kinetics of propane dehydrogenation in this model, the kinetic form and values for a chromium-oxide based catalyst were obtained from the publication of J. Gascón, C. Téllez, J. Herguido and M. Menéndez, *Applied Catalysis A: General*, Volume 248, Issues 1-2, 8 Aug. 2003, pages 105-116. The kinetics of catalytic methane combustion within the dehydrogenation catalyst bed were taken from the publication of S. Ordonez et al. *Applied Catalysis A: General*, Volume 341 (2008), pages 174-180, for a Chromium based catalyst. The kinetics of non-catalyzed (thermal) methane combustion were estimated from M. van Sint Annaland et al., *Chemical Engineering Science*, 57, (2002), pp. 833-854 (part I) and pp. 855-872 (part II), and were included in our overall simulation.

Figure 3A:
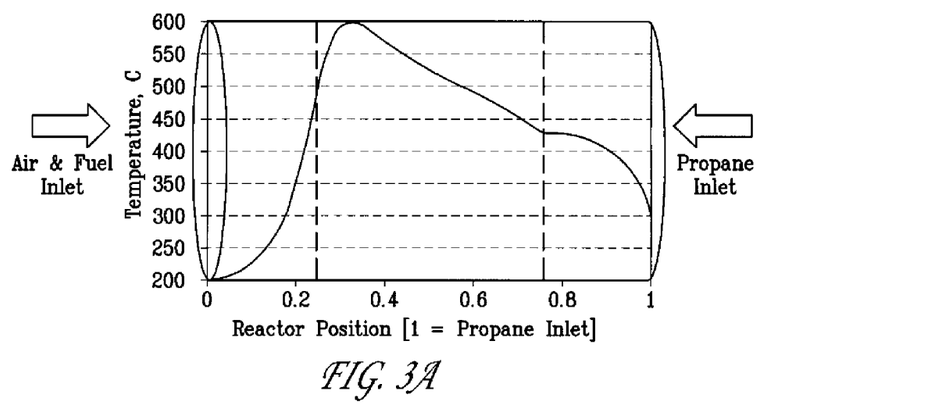
FIG. 3A is a graphic representation of the temperature profile across an RFR according to the base case of FIG. 1C.

For a realistic set of gas flows, a cycle-average temperature profile for the base case was obtained as shown in FIG. 3A. Note that the temperature profile (moving from right to left, with the propane flow direction in this figure) reaches a maximum of 600° C. at around x=0.32. From that point on, the temperature in the bed drops steeply, falling to 500° C. at the exit of the catalyst bed at x=0.25.

Figure 3B:
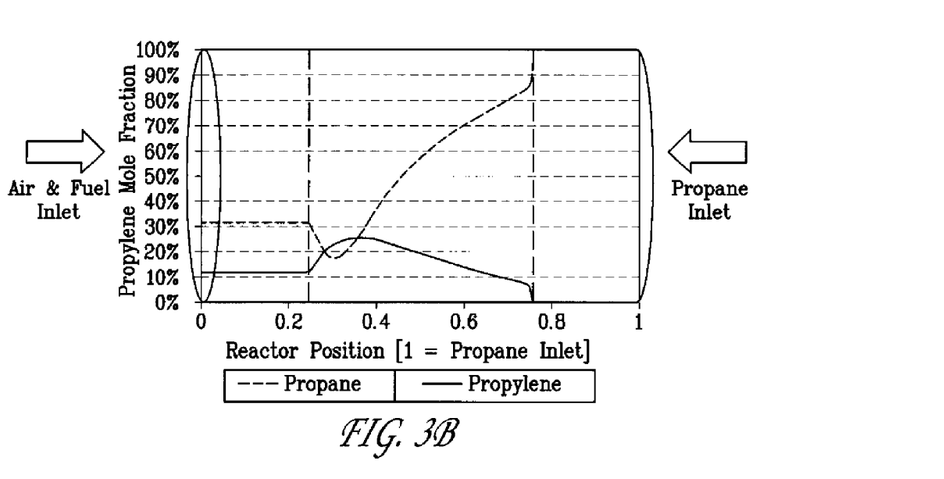
FIG. 3B is a graphic representation of propane/propylene mole fractions across an RFR according to FIG. 3A.

The consequences of this drop-off in temperature are illustrated in FIG. 3B. This shows the propylene mole fraction in the reaction gases. The propylene reaches a maximum of 26% in the bed, near the temperature peak at around x=0.35. However, as the reaction gases traverse the cooler zone at the end of the dehydrogenation catalyst bed, some propylene gets converted back into propane, and the propylene mole fraction drops to 12% at the exit.

Example 2

In Example 2 (Disclosure), the same gas flows and dehydrogenation catalyst kinetics were used as in Example 1. The difference here is that a selective combustion catalyst was added from x=0.23 to x=0.25. The catalytic methane combustion kinetics for this material were obtained from Uasuda et al., *Journal of Material Science* 46 (2011) 4046-4052 for a $PdO/CZB/Al_2O_3$ catalyst.

Figure 4A:
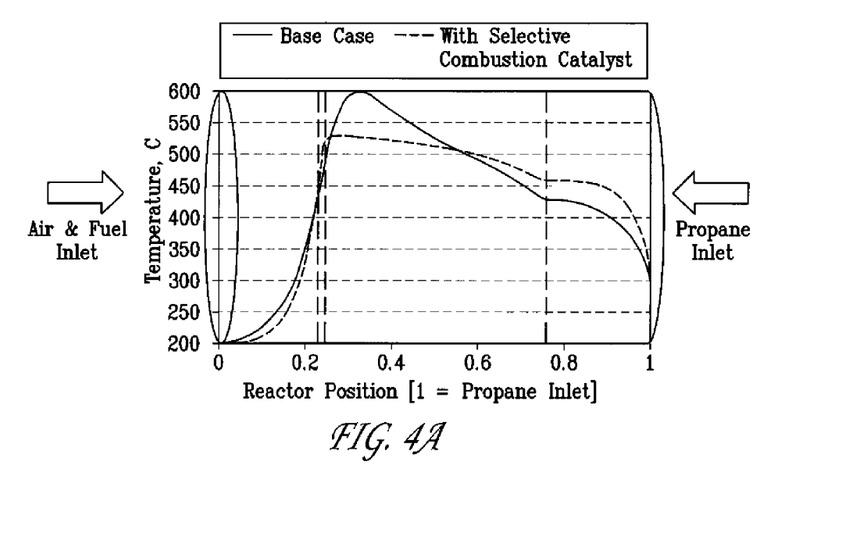
FIG. 4A is a graphic representation of the temperature profile across an RFR comparing the base case of FIG. 3A to an RFR comprising the improvement disclosed herein.
Figure 4B:
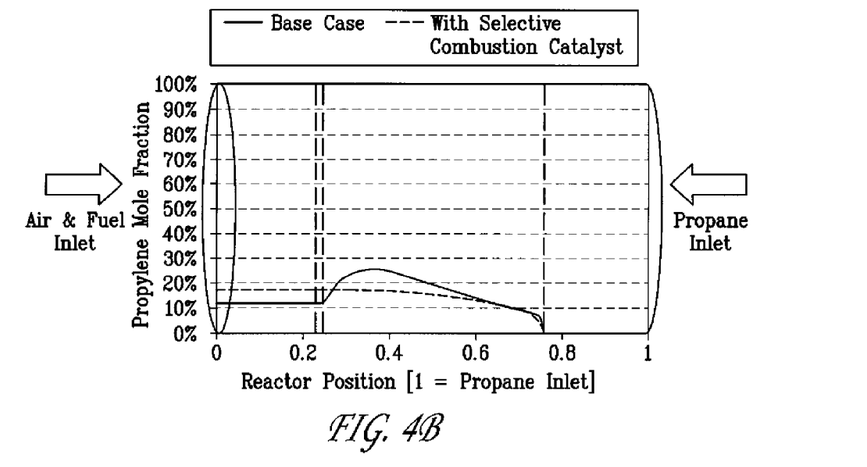
FIG. 4B is a graphic representation of propane/propylene mole fractions across an RFR comparing the base case of FIG. 3B to an RFR comprising the improvement disclosed herein.

Essentially complete combustion of the methane fuel gas is obtained in the selective combustion bed. The resulting temperature profile is compared to the base case temperature profile in FIG. 4A. Now a monotonically rising (from right to left) temperature profile is obtained in the dehydrogenation catalyst bed. The propylene yield profile with the selective combustion bed (Example 2) is compared in FIG. 4B to the base case (Example 1). Now propylene yields rise steadily through the catalyst bed. The peak temperature for Example 2 (at x=0.26) is lower than for Example 1, and thus fewer undesired byproducts are formed. The net result is that the propylene yield at the reactor exit is 18% for Example 2 (selective catalyst bed added) as opposed to 12% for the base case (Example 1).

We have discussed above a specification of the minimum oxidation activity of the selective combustion catalyst: it must accomplish the combustion of at least 40%, preferably at least 60%, and more preferably at least 85% of the fuel gas provided during the regeneration phase of the reverse flow operation, with the chosen combustion bed length or reactor volume fraction.

We also specify another constraint on this catalyst, having to do with its activity in hydrogenation. The reason for this is that there may be a non-monotonic temperature profile within the selective combustion zone. This has the potential to reverse the dehydrogenation of the paraffin. A key to preventing this is to maintain the hydrogenation activity of this selective combustion catalyst at a suitably low level. The absolute value of the hydrogenation activity needed here depends on the amount of selective combustion catalyst loaded in the reactor, which in turn depends on the oxidation activity of that catalyst. If the combustion catalyst is very active in oxidation, then only a small amount of it need be loaded in the reactor to accomplish combustion of the fuel, and so (unless its hydrogenation activity per volume is also very high) the problem of back-conversion of propylene in the reactor becomes negligible. Thus, the requirement for low back-conversion in the selective combustion bed may be expressed as a ratio of the activity of the catalyst for oxidation to its activity for hydrogenation, or more conveniently as the following ratio: (percent fuel oxidation per unit volume of catalyst)/(percent olefin hydrogenation per unit volume of catalyst).

A set of simulations was performed to quantitatively explore this issue, and to define the range of activity ratios that give the desired low back-conversions. In the simulations, the combustion activity is quantified during a combustion step as the percent conversion of methane per selective combustion catalyst bed volume. Likewise, the hydrogenation activity is quantified during a dehydrogenation step as the as the propylene-back-conversion to propane (expressed as a percent of the initial feed propane) per selective combustion catalyst bed volume. The ratio of relative reactivities for the selective combustion catalyst is defined as the ratio of combustion activity to hydrogenation activity. This ratio of relative reactivities has been found to correlate with the amount of propylene back conversion that occurs. It is found that when the methane or combustion fuel conversion per selective combustion catalyst volume is 2.9 times greater than the propylene conversion per selective combustion catalyst volume, there is back conversion of propylene in the amount of approximately 5% of the initial propane feed. Also keeping the activity ratio above 3.3 ensures that propylene (or e.g. ethylene or butene, if the feed to the dehydrogenation reactor were ethane or butane, respectively) back conversion will be kept below 1% of the original feed. Although this study was done for just one set of kinetics and flow rates, the same type of relationship should hold in general between this ratio and the amount of undesired back conversion. For the selective catalyst bed of this disclosure, it is preferred to maintain this ratio greater than 2.5, and more preferred greater than 3.3. For example, in the quantitative Example 2, the ratio is 3.4. The oxidation conversion and the back-conversion of propylene are evaluated at the actual conditions of reactor operation, during the regeneration and the dehydrogenation phases, respectively. These conversions may be directly measured in an operating reactor, or calculated from a transient reactor model.

A practical advantage to defining the selective catalyst requirements in this manner is that potential selective combustion catalysts can be screened in conventional fixed-bed laboratory reactors. For a fixed amount of catalyst, the percentage of fuel gas combustion could be measured, with temperature, pressure, and space velocity of the fuel/air mixture fixed at the values expected in the full-scale reactor. The dehydrogenation reaction would likewise be measured using an olefin/hydrogen mixture that approximates the mixture, conditions, and space velocity expected at the exit of the main dehydrogenation catalyst bed. The olefin would be the dehydrogenation product of the main feed to the dehydrogenation reactor. For instance, for propane feed, the olefin in this test reaction would be propylene. It is not necessary to match the actual product mixture exactly, since percent conversion (of propylene to propane) is the key measurement, as opposed to an absolute measurement of moles per unit volume per unit time. It is preferred that the ratio of [percentage fuel gas oxidation]/[percentage feed olefin saturation] be greater than 2, and more preferred to be greater than 5.

Some preferred materials for the selective combustion catalysts include oxides and mixed oxides of the metals in columns IIIB through VA, plus the lanthanides. Controlled amounts of precious metals (column VIII in periodic table), especially Pd, are also preferred. The metals or metal oxides may be supported on a porous, thermally stable support. Some suitable supports include alumina, silica, zirconia, and magnesia.

All documents described herein are incorporated by reference herein, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. Likewise, the term "comprising" is considered synonymous with the term "including" for purposes of Australian law.

When numerical lower limits and numerical upper limits are listed herein, ranges from any lower limit to any upper limit are contemplated.

While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

What is claimed is:

1. A process comprising:
providing a reverse flow regenerative reactor comprising separate first and second zones and a combustion zone between said first and second zones, both of said first and second zones having first and second ends, and comprising a plurality of channels and wherein said first zone is configured to transfer heat to or from gases passing therethrough, and at least a portion of said second zone comprises a dehydrogenation catalyst;
passing at least two components of a combustible gas mixture in a first direction through said first zone, wherein substantially all of the at least two components are passed as a mixture and not passed separately through mutually exclusive channels;
combusting said combustible gas mixture with the aid of a selective combustion catalyst disposed in said combustion zone to form hot combustion products wherein the selective combustion catalyst is disposed on channels at the second end of the first zone, in a catalyst bed downstream of the second end of the first zone, or on a support at the first end of the second zone separated from and upstream of the portion of the second zone comprising a dehydrogenation catalyst;

passing said hot combustion products through said second zone to transfer heat from said hot combustion products to said dehydrogenation catalyst, so as to heat said dehydrogenation catalyst to a selected temperature; and exhausting said combustion products from said second zone, wherein a ratio of combustion activity to hydrogenation activity for the selective combustion catalyst is greater than 2.5, and wherein the selective combustion catalyst results in a combustion of at least 40% of a fuel gas in the combustible gas mixture.

2. The process of claim 1, further comprising:
terminating gas flow in said first direction;
passing a hydrocarbon feed comprising $C_1$-$C_{10}$ hydrocarbons in a direction opposite said first direction and into the second end of said second zone;
dehydrogenating at least a portion of said hydrocarbon feed within said second zone to form one or more dehydrogenated hydrocarbon products;
passing said dehydrogenated hydrocarbon products into the second end of said first zone and quenching said dehydrogenated hydrocarbon products; and
recovering said dehydrogenated hydrocarbon products from the first end of said first zone.

3. The process of claim 1, wherein said dehydrogenation catalyst comprises Group VB metals, Group VIB metals, Group VIII metals, Group VIII metal alloys with Group IB metals, or oxides thereof.

4. The process of claim 2, wherein the dehydrogenation is conducted at a selected temperature from 625° C. to 800° C., and a pressure from 1 to 5 atmospheres.

5. The process of claim 2, wherein said hydrocarbon feed is propane and said dehydrogenated hydrocarbon product is propylene.

6. The process of claim 2, wherein said hydrocarbon feed is butane and said dehydrogenated hydrocarbon product is butenes and/or butadiene.

7. The process of claim 2, wherein dehydrogenation process is a dehydrocyclodimerization process, wherein said hydrocarbon feed is $C_1$-$C_{10}$ paraffins or olefins, further comprising dimerizing or further oligomerizing said dehydrogenated hydrocarbon product(s) to form aromatic hydrocarbons.

8. The process of claim 7, further comprising a dehydrocyclodimerization catalyst disposed on a support within said second zone.

9. The process of claim 8, wherein said dehydrocyclodimerization catalyst comprises a ZSM-5 medium-pore molecular sieve promoted with a dehydrogenation function including Ga, Pt, Zn, In, Pd, Ir, Mo or combinations thereof.

10. The process of claim 2, wherein the hydrocarbon feed is light virgin naphtha having $C_4$-$C_{10}$ paraffins, and further comprises cracking of said feed to increase the yield of light olefins in the product.

11. The process of claim 2, wherein hydrogen derived from said dehydrogenation step is recycled to the reaction to improve selectivity of the reaction step for various products.

12. The process of claim 1, wherein the selective combustion catalyst comprises oxides of metals in columns IIIB through VA of the periodic table, including lanthanides, and combinations thereof.

13. The process of claim 12, wherein the selective combustion catalyst is a basic catalyst.

14. The process of claim 1, wherein the combustion zone further comprises an inert packing or support, capable of retaining heat.

15. The process of claim 1, wherein the plurality of channels of said first and second zones comprise ceramics.

* * * * *